US00RE50896E

(19) United States
(12) Reissued Patent
Blackwell

(10) Patent Number: US RE50,896 E
(45) Date of Reissued Patent: May 26, 2026

(54) APPARATUS FOR TESTING A LIQUID SPECIMEN

(71) Applicant: CLINICAL DESIGN TECHNOLOGIES LIMITED, Devon (GB)

(72) Inventor: Oliver Blackwell, Devon (GB)

(73) Assignee: Clinical Design Technologies Limited, Devon (GB)

(21) Appl. No.: 18/491,169

(22) Filed: Oct. 20, 2023

Related U.S. Patent Documents

Reissue of:
(64) Patent No.: 11,161,117
Issued: Nov. 2, 2021
Appl. No.: 15/513,071
PCT Filed: Oct. 10, 2015
PCT No.: PCT/GB2015/000285
§ 371 (c)(1),
(2) Date: Mar. 21, 2017
PCT Pub. No.: WO2016/066983
PCT Pub. Date: May 6, 2016

(30) Foreign Application Priority Data

Oct. 27, 2014 (GB) ..... 1419133

(51) Int. Cl.
*B01L 3/00* (2006.01)
*A61B 10/00* (2006.01)

(52) U.S. Cl.
CPC ..... *B01L 3/50825* (2013.01); *A61B 10/007* (2013.01); *B01L 3/5023* (2013.01);
(Continued)

(58) Field of Classification Search
CPC ..... A61B 10/007; A61B 2010/0006; A61B 2010/0003; B01L 3/05825; B01L 3/5023;
(Continued)

(56) References Cited

U.S. PATENT DOCUMENTS 5,119,830 A 6/1992 Davis
5,595,187 A * 1/1997 Davis ..... A61B 10/007 600/573

(Continued)

FOREIGN PATENT DOCUMENTS

JP 2007-278926 A 10/2007
WO 97/35512 A1 10/1997
WO 2011157981 A1 12/2011

OTHER PUBLICATIONS

"Bevel Pins Piercing Heads", V&P Scientific, Product description bevel pins, 2010, 1 page.

(Continued)

*Primary Examiner* — Elizabeth L McKane
(74) *Attorney, Agent, or Firm* — Nicholas J. Landau; Maynard Nexsen PC

(57) ABSTRACT

Apparatus (2) for testing a liquid specimen, which apparatus (2) comprises: (i) a container (4) for the liquid specimen; (ii) a lid (6) for closing the container (4) after the liquid specimen has been provided in the container (4); (iii) first securing means (8) by which the lid (6) is secured to the container (4); (iv) a test capsule (10) for securing to the lid (6) when the lid (6) is on the container (4); (v) second securing means (12) by which the test capsule (10) is secured to the lid (6); and (vi) a response chart (14) which is operable in response to contact with the liquid specimen, and the apparatus (2) being such that: (vii) the lid has an openable portion (18) which when opened permits a liquid specimen in the container (4) to enter the test capsule (10); (viii) the test capsule (10) has opener means (20) for opening the openable portion on the lid (6) when the test capsule (10) is secured to the lid (6); and (ix) the response chart (14) is inside the test capsule (10) and is contacted by the liquid specimen when the liquid specimen enters the test capsule (10).

34 Claims, 6 Drawing Sheets

(52) U.S. Cl.
CPC ..... *A61B 2010/0003* (2013.01); *A61B 2010/0006* (2013.01); *B01L 2200/023* (2013.01); *B01L 2200/0615* (2013.01); *B01L 2300/025* (2013.01); *B01L 2300/042* (2013.01); *B01L 2300/044* (2013.01); *B01L 2300/046* (2013.01); *B01L 2300/047* (2013.01); *B01L 2300/0627* (2013.01); *B01L 2300/0672* (2013.01); *B01L 2300/0803* (2013.01); *B01L 2300/0825* (2013.01); *B01L 2300/0832* (2013.01)

(58) Field of Classification Search
CPC ..... B01L 2300/0627; B01L 2300/046; B01L 2300/044; B01L 2300/0825; B01L 2300/025; B01L 2300/0672; B01L 2300/0832; B01L 2300/042; B01L 2300/047; B01L 2300/0803; B01L 2200/0615; B01L 2200/023
See application file for complete search history.

(56) References Cited

U.S. PATENT DOCUMENTS

| | | | | |
|---|---|---|---|---|
| 5,711,453 | A * | 1/1998 | Weiler | B65D 47/14 222/541.2 |
| 6,477,743 | B1 * | 11/2002 | Gross | B65D 51/226 222/499 |
| 8,201,700 | B2 * | 6/2012 | Shibata | B65D 47/36 215/331 |
| 2011/0044856 | A1 | 2/2011 | Wong et al. | |
| 2013/0089474 | A1 * | 4/2013 | Blackwell | G01N 33/523 422/402 |

OTHER PUBLICATIONS

Search Report received for Chinese Patent Application No. 201580055307.4, mailed on Oct. 19, 2018, 2 Pages.
First Office Action received for Chinese Patent Application No. 201580055307.4, mailed on Oct. 29, 2018, 17 Pages including English Translation.
Second Office Action received for Chinese Patent Application No. 201580055307.4, mailed on Aug. 19, 2019, 18 Pages including English Translation.
Third Office Action received for Chinese Patent Application No. 201580055307.4, mailed on Apr. 1, 2020, 8 Pages including English Translation.
Office Action received for European Patent Application No. 15787655.8, mailed on Nov. 12, 2018, 4 Pages.
Office Action received for European Patent Application No. 15787655.8, mailed on Jun. 25, 2018, 5 Pages.
Search Report received for Japanese Patent Application No. 2017-519572, mailed on May 16, 2019, 15 Pages including English Translation.
Notice of Reasons for Refusal received for Japanese Patent Application No. 2017-519572, mailed on Jun. 11, 2019, 4 Pages including English Translation.
International Search Report and Written Opinion received for International Application No. PCT/GB2015/000285, mailed on Jan. 21, 2016, 11 pages.
International Preliminary Report on Patentability received for International Application No. PCT/GB2015/000285, mailed on May 11, 2017, 8 pages.
V&P Scientific, Product description bevel pins, 2010 (Year: 2010).*

* cited by examiner

APPARATUS FOR TESTING A LIQUID SPECIMEN

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This is a reissue of U.S. Pat. No. 11,161,117, filed on Mar. 27, 2017 (issued); which is a national stage of PCT/GB2015/000285, filed on Oct. 10, 2015; which cites the priority of United Kingdom Patent Number GB1419133 (abandoned).*

This invention relates to apparatus for testing a liquid specimen.

Apparatus for testing liquid specimens is well known. If the liquid specimen is in the form of urine, then a dipstick is usually used to test the urine. The testing of urine with a dipstick is carried out many times a day in medical practices clinics and hospitals around the world. The testing of the urine is essential in the diagnosis of urinary tract infections, for screening for protein and blood in the urine, and for the diagnosis of many other conditions.

The standard way in which the urine is tested with a dipstick involves a patient filling a container with urine, and then handing the container to an authorised person such for example as a nurse, a technician or a doctor. The authorised person is required to dip the dipstick into the urine in the container, wiping off excess urine on the rim of the container. The dipstick has response portions which are contacted by the liquid specimen, which become differently coloured to indicate different characteristics, present in the urine, and which are read at predetermined time periods. The response portions are read against a result chart at predetermined time intervals of up to two minutes. The entire procedure may take a minimum of three minutes to perform effectively. The procedure is unhygienic and is prone to error if the response portions are read at incorrect time intervals.

WO 2011/157981 A1 addresses the above problems. More specifically, WO 2011/157981 A1 discloses apparatus for testing a liquid specimen, with the apparatus comprising a container for the liquid specimen, a response chart which is operable in response to contact with the liquid specimen, and a result chart for use with the response chart. The apparatus is such that the response chart is in the container. In normal use, the container is provided to a patient. A problem can arise in that the containers are used in large quantities due to there being large numbers of patients. It often happens that patients mislay the containers and require further containers. Whilst the containers are not overly expensive in themselves, the mislaying of substantial numbers of containers represents a significant cost to a medical practice. This cost would best be avoided.

It is an aim of the present invention to reduce the above mentioned problem.

Accordingly, the present invention for provides apparatus for testing a liquid specimen, which apparatus comprises:

(i) a container for the liquid specimen;

(ii) a lid for closing the container after the liquid specimen has been provided in the container;

(iii) first securing means by which the lid is secured to the container;

(iv) a test capsule for securing to the lid when the lid is on the container;

(v) second securing means by which the test capsule is secured to the lid; and (vi) a response chart which is operable in response to contact with the liquid specimen, and the apparatus being such that:

(vii) the lid has an openable portion which when opened permits a liquid specimen in the container to enter the test capsule;

(viii) the response chart is inside the test capsule and is contacted by the liquid specimen when the liquid specimen enters the capsule;

(ix) the test capsule has opener means for opening the openable portion on the lid;

and the apparatus being characterised in that:

(x) the opener means is not able to move with respect to the test capsule, wherby the opener means opens the openable portion when the test capsule is being secured to the lid, and whereby the opener means remains unmoved with respect to the test capsule both before and after the openable portion has been opened by the opener means; and (xi) the opener means is a cylinder having a longitudinal axis which extends along a longitudinal axis of the apparatus.

The apparatus of the present invention is advantageous in that only the container and the lid need to be provided in bulk to patients. The cost of the container and the lid is relatively inexpensive when compared with the container with its response chart as disclosed in WO 2011/157981 A1. With the apparatus of the present invention, the test capsule is the significant part of the cost of the entire apparatus, and this test capsule is able to be retained by a medical practice, hospital or other organisation. Thus the test capsule is not sent to patients and is thus not subject to being lost. Cost saving are thus able to be made.

The first securing means may be a screw-operated first securing means. Other types of first securing means may be employed so that, for example, the first securing means may be a push fit first securing means.

The second securing means may be a push fit securing means. Other second securing means may be employed so that, for example, the second securing means may be a screw fit second securing means.

Preferably, the second securing means causes the test capsule to be permanently secured to the lid in order to minimise the possibility of spillage of the liquid specimen.

The second securing means may comprise an outwardly extending formation on the container, and an inwardly extending formation on the test capsule. The outwardly extending formation on the container may be a lip which is angled outwardly away from a top of the container. Other types of outwardly extending formation may be employed.

The inwardly extending formation on the test capsule may be an inclined bead formation. Other types of inwardly extending formation may be employed.

The openable portion of the lid may be a foil or a membrane. Other types of openable portion may be employed.

The opener means of the test capsule may be a puncturing formation for puncturing the openable portion of the lid. The puncturing formation may be a cylindrical formation having a free end which extends at an angle to the openable portion of the lid. Other puncturing formations may be employed so that, for example, the puncturing formation may be one or more pins. The cylindrical formation with the free end which extends at an angle to the openable portion of the lid is preferred because the free end forms a point for opening purposes. The part opposite the free end has a flat section which prevents the formation of a complete cut circle. This flat section causes a hinge to be created in the punctured openable portion. This flat section also passes through the, openable portion and holds open the punctured portion of the openable portion parallel to the longitudinal axis of the test capsule, thereby ensuring that the openable portion does not interrupt the urine flow.

The apparatus may include a result chart for use with the response chart. In this case, the result chart is preferably outside of the test capsule. The result chart may fit on the test capsule. When the result chart fits on the test capsule, then the apparatus may be one in which the result chart has a central aperture, in which the test capsule has a reduced portion and a shoulder, and in which the result chart fits over the reduced portion and abuts against the shoulder.

The apparatus may be one in which the result chart comprises result sectors, each result sector is for indicating the result of a different test for the liquid specimen, and each result sector has a plurality of differently coloured result portions, and the different colours of the result portions in each result sector indicate different degrees of result for the test afforded by the result sector. The result sectors may be arranged in a circle. The result sectors may be otherwise arranged if desired.

As an alternative to the apparatus including a result chart for use with the response chart, the apparatus of the present invention may be one in which the results are obtained electronically, for example using digital read-out result means.

The apparatus may be one in which the container is a tube of a diameter for fitting into laboratory test equipment. In this case, the tube may be a test tube or a primary tube. A primary tube is a test tube but with a screw thread for receiving a lid.

The apparatus may be one in which the response chart comprises response portions which are contacted by the liquid specimen, which become differently coloured to indicate different characteristics present in the liquid specimen, and which are read at predetermined time intervals. The response portions may be arranged in a circle. The response portions may be arranged other than in a circle if desired.

The apparatus may be one in which the response chart is inside the test capsule such that the response chart is in a test chamber.

The apparatus may include aligning means for aligning one of the result sectors with one of the response portions such that each one of the result sectors has it own one of the response portions.

The apparatus may be one in which the cylinder has a diameter such that when the test capsule is secured to the lid, walls defining the cylinder are adjacent walls defining the container, whereby the opener means opens the openable portion over substantially the entire diameter of the container and thereby allows maximum flow of the liquid specimen from the container into the test capsule.

The apparatus of the present invention may be used for testing a wide variety of liquid specimens. Usually the liquid specimens will be body fluid liquid specimens but other liquid specimens may be tested. Where the liquid specimens are body fluid liquid specimens, then the liquid specimens may be urine, blood or spinal fluid.

Embodiments of the invention will now be described solely by way of example and with reference to the accompanying drawings in which.

Figure 1:
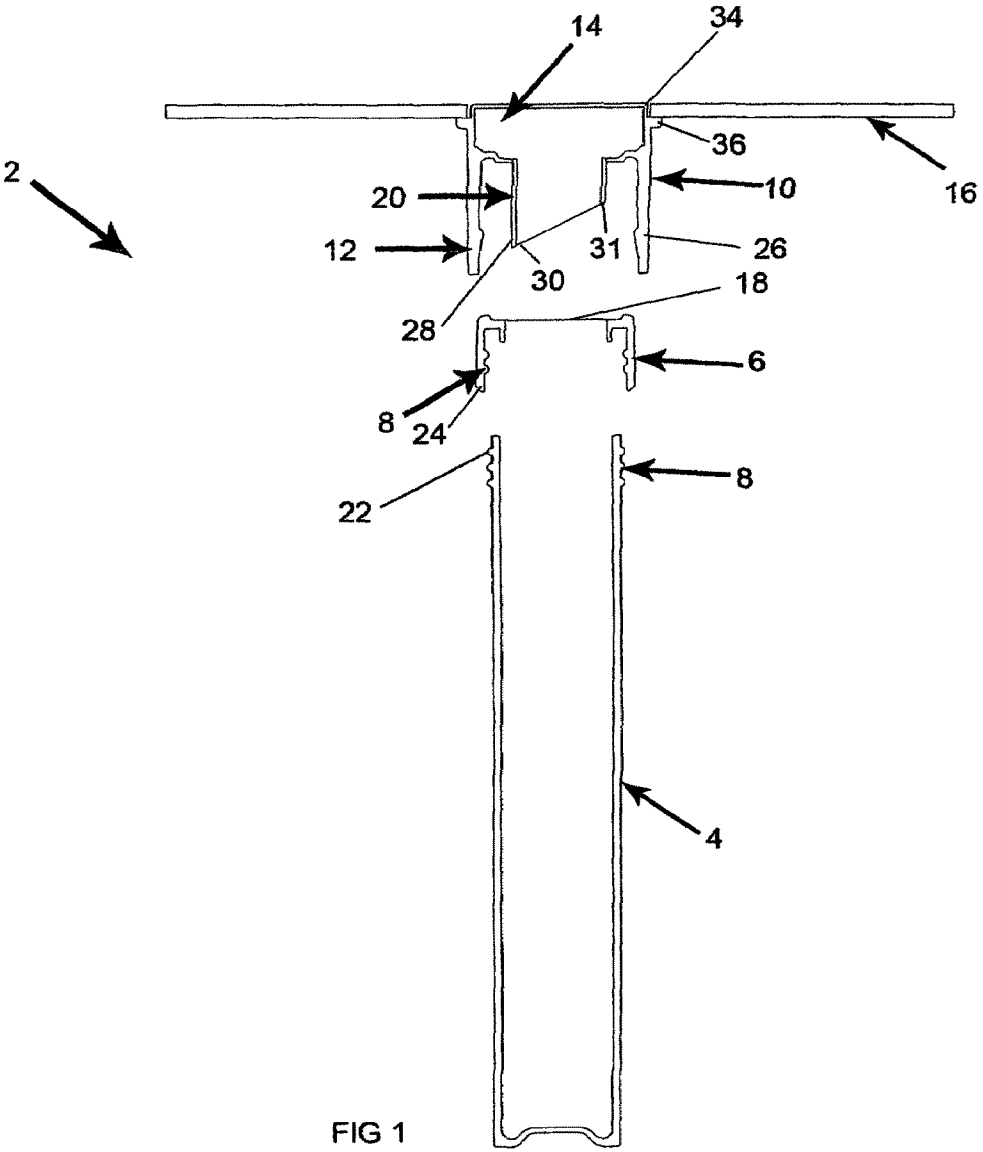
FIG. 1 is an exploded view of first apparatus for testing a liquid specimen.

Referring to FIGS. 1-6, there is shown apparatus 2 for testing a liquid specimen. The apparatus 2 comprises a container 4 for the liquid specimen. The apparatus 2 also comprises a lid 6 for closing the container 4 after the liquid specimen has been provided in the container 4. First securing means 8 enables the lid 6 to be secured to the container 4.

The apparatus 2 further comprises a test capsule 10 for securing to the lid 6 when the lid 6 is on the container 4. The second securing means 12 enables the test capsule 10 to be secured to the lid 6.

The apparatus 2 further comprises a response chart 14 which is operable in response to contact with the liquid specimen. A result chart 16 is provided for use with the response chart 14.

The apparatus 2 is such that the lid 6 has an openable portion 18 which when opened permits the liquid specimen in the container 4 to enter the test capsule 10. The test capsule 10 has opener means 20 for opening the openable portion 18 on the lid 6 when the test capsule 10 is secured to the lid 6. The response chart 14 is inside the test capsule 10 and is contacted by the liquid specimen when the liquid specimen enters the test capsule 10. The result chart 16 is outside of the test capsule 10.

The first securing means 8 is a screw-operated first securing means 8 and, as shown, comprises internal threads on the lid 6 and external threads on the container 4. Thus the lid 6 screws to a top 22 of the container 4.

Figure 4:
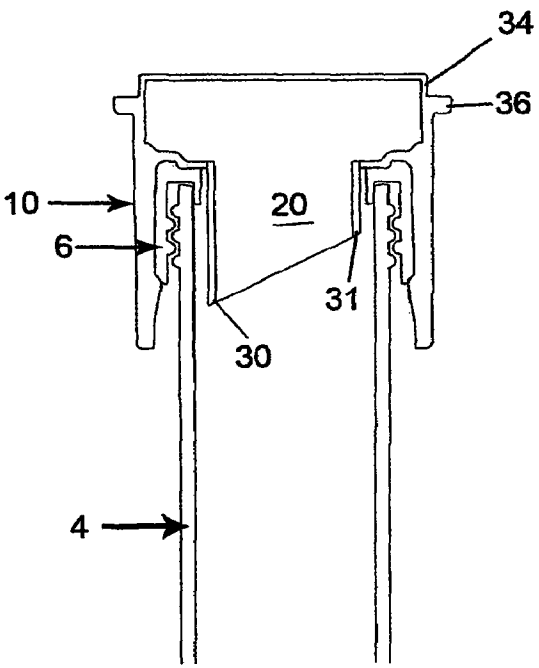
FIGS. 2, 3 and 4 show how the apparatus shown in FIG. 1 is progressively assembled.
Figure 3:
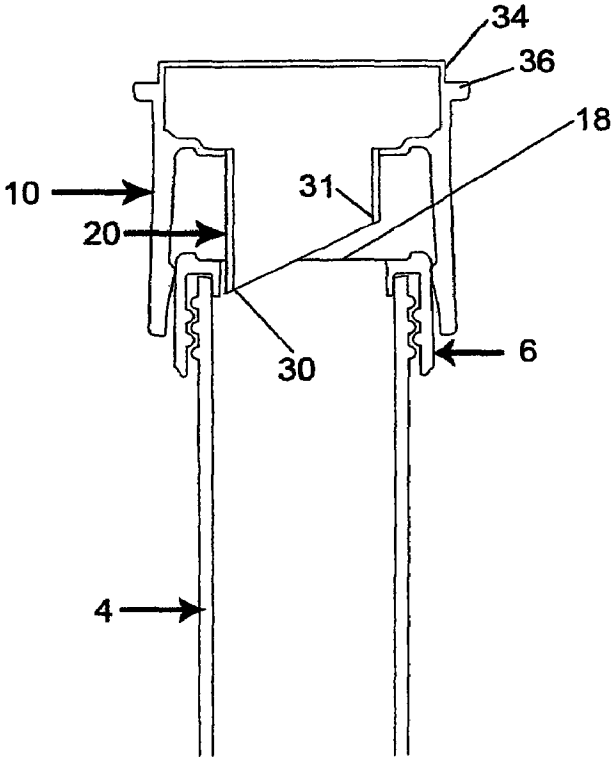
Figure 2:
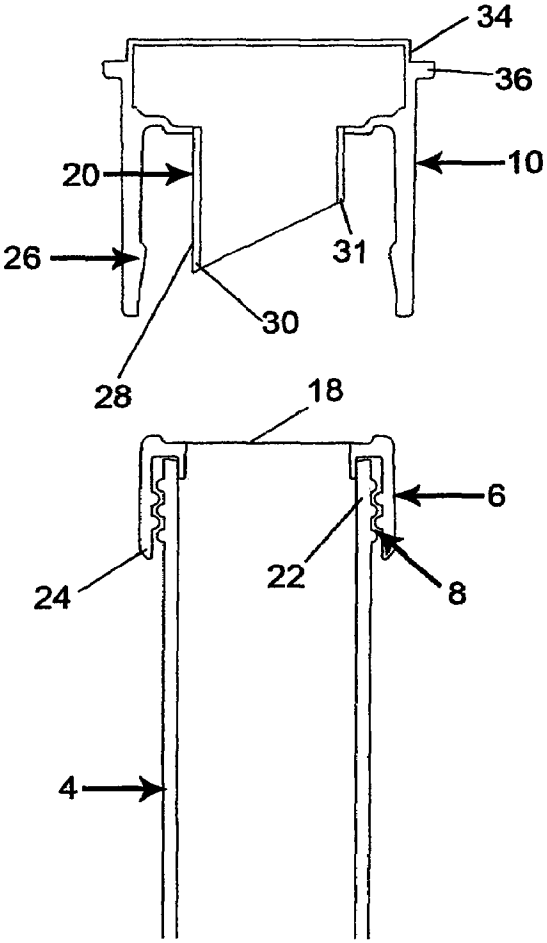
Figure 6:
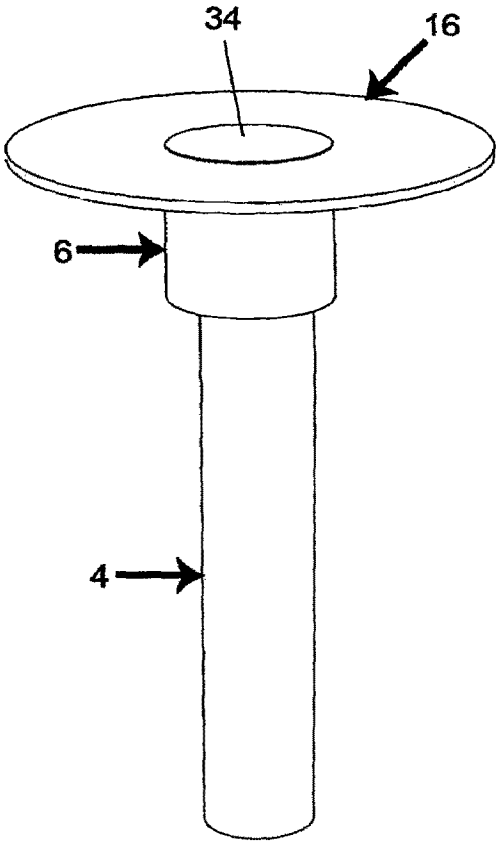
FIG. 6 is a perspective view of the assembled apparatus as shown in FIG. 4.
Figure 5:
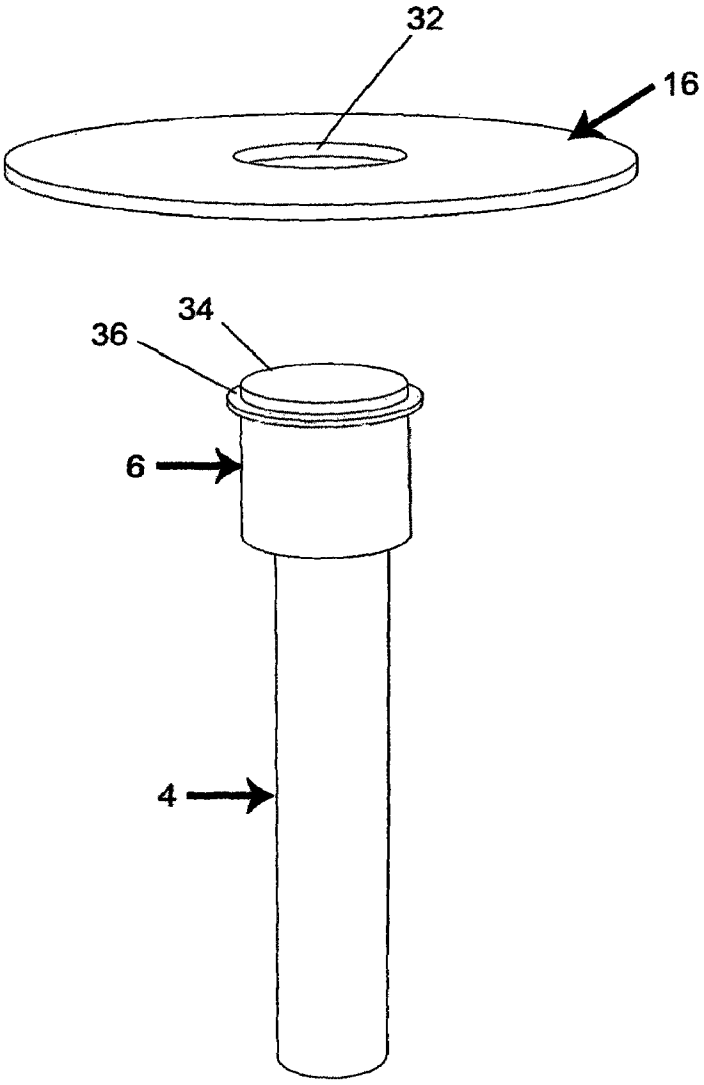
FIG. 5 is an exploded perspective view of the apparatus as shown in FIG. 2.

The second securing means 12 is a push fit securing means 12. Thus the second securing means 12 is a push fit over the lid 6 as shown in FIGS. 3 and 4.

The openable portion 18 of the lid 6 is a foil. The openable portion 18 may alternatively be a membrane or other member.

The opener means 20 of the test capsule 10 has a puncturing formation for puncturing the openable portion 18 of the lid 6. The puncturing formation is a cylindrical formation 28 having a free end 30 which extends at an angle to the openable portion 18 of the lid 6 as shown. The free end 30 provides a focussing opening force at a point to puncture the openable portion 18 of the lid 6. The part 31 opposite the free end 30 has a flat section which prevents the formation of a complete cut circle. This flat section causes a hinge to be created in the punctured openable portion 18. This flat section also passes through the openable portion 18 and holds open the punctured portion of the openable portion 18 parallel to the longitudinal axis of the test capsule 10, thereby ensuring that the openable portion 18 does not interrupt the urine flow.

The result chart 16 fits on the test capsule 10. This can best be appreciated from a comparison of FIGS. 5 and 6. The result chart 16 has a central aperture 32. The test capsule 10 has a reduced portion 34 and a shoulder 36. The result chart 16 fits over the reduced portion 34 and abuts against the shoulder 36.

The container 4 may be a test tube or what is known as a primary tube in the field of medical diagnostics.

The response chart 14 comprises response portions 38 which are contacted by the liquid specimen, which become differently coloured to indicate different characteristics present in the liquid specimen, and which are read at predetermined time intervals.

Figure 7:
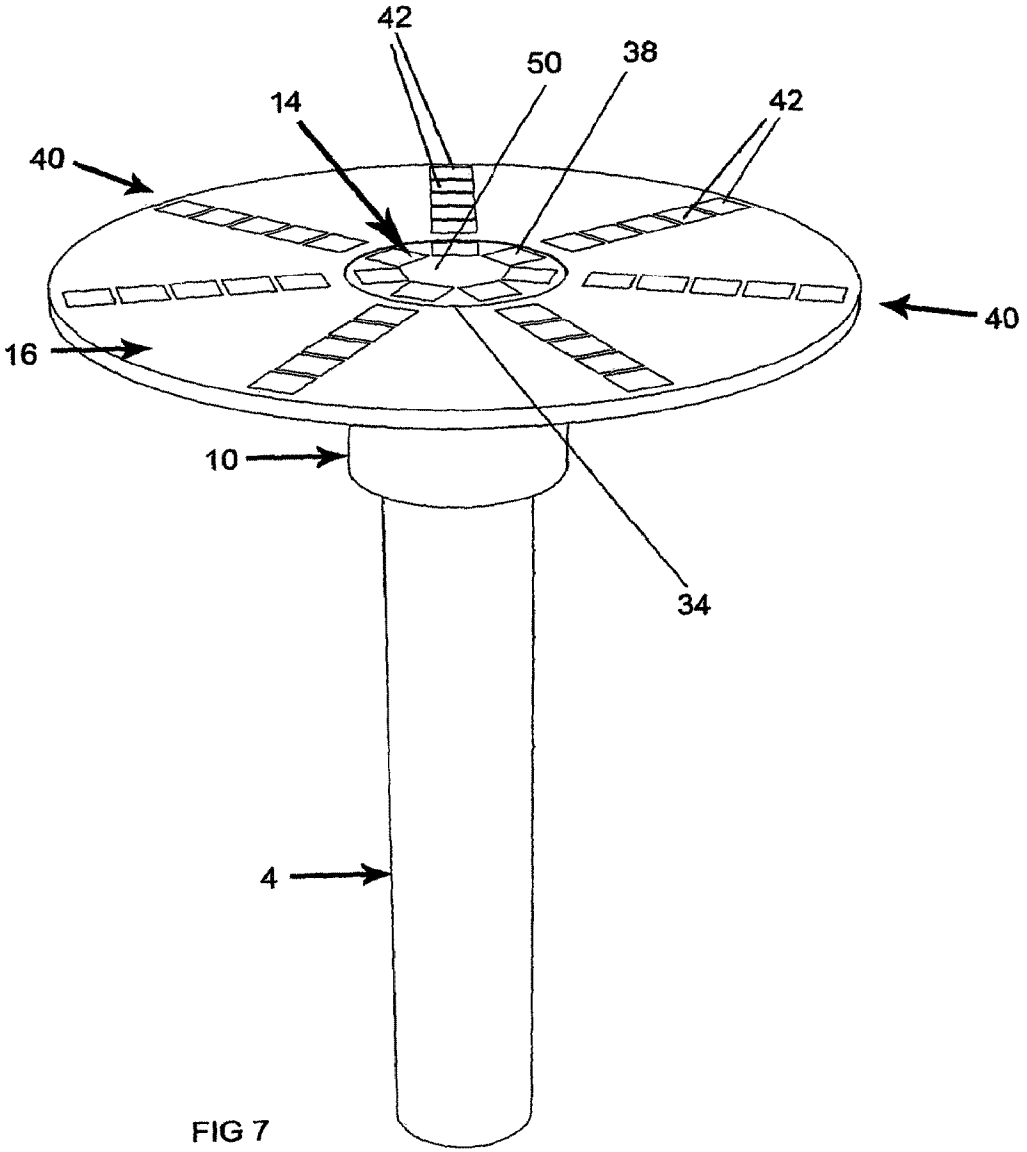
FIG. 7 is a top perspective view of the apparatus as shown in FIG. 6 and shows in more detail a preferred result chart.

Referring to FIG. 7, there is shown a preferred result chart 16. The result chart shown in FIG. 7 comprises result sectors 40 for indicating the result of a different test for the liquid specimen. Each result sector 40 has a plurality of differently coloured result portions 42. The different colours of the result portions 42 in each result sector 40 indicate different degrees of result for the rest afforded by the result sector 40.

The apparatus 2 includes aligning means (not shown) for aligning one of the result sectors 40 with one of the response portions 38 such that each one of the result sectors 40 has its own one of the response portions 38.

The response chart 14 is inside the test capsule 10 such that the response chart 14 is in a test chamber 50. The response portions 38 are arranged in a circle. The result sectors 40 are arranged in a circle.

Figure 9:
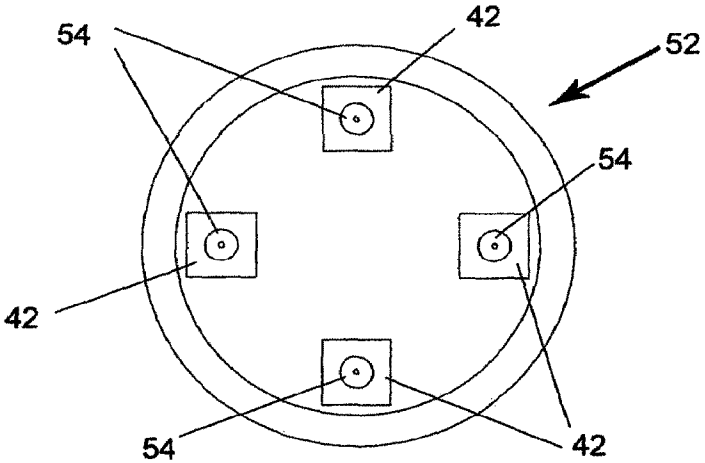
FIGS. 8 and 9 are sectional and top plan views of a first type of test capsule.
Figure 8:
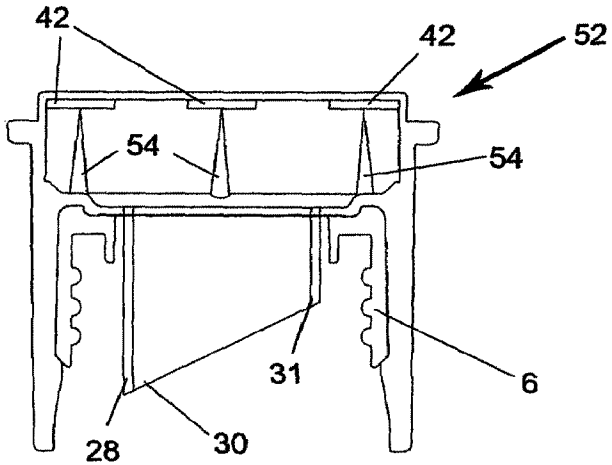

FIGS. 8 and 9 show a test capsule 52 having result portions 42 mounted on conical pins 54.

Figure 11:
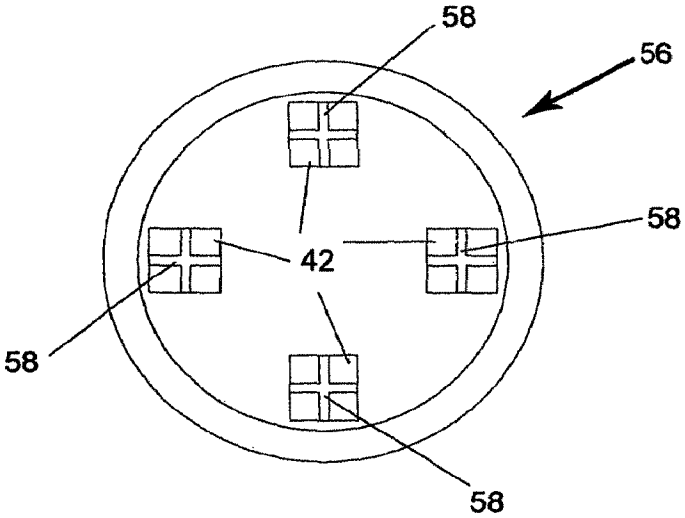
FIGS. 10 and 11 are sectional and top plan views of a second type of test capsule.
Figure 10:
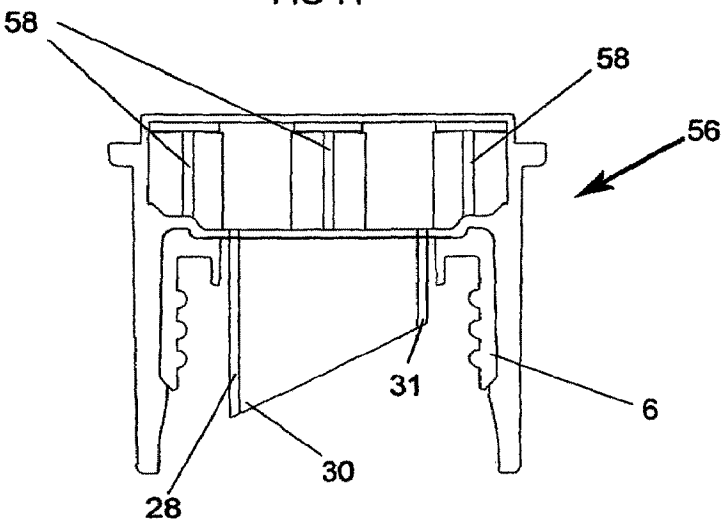

FIGS. 10 and 11 show a test capsule 56 with result portions 42 supported by cross-shaped pins 58.

Figure 13:
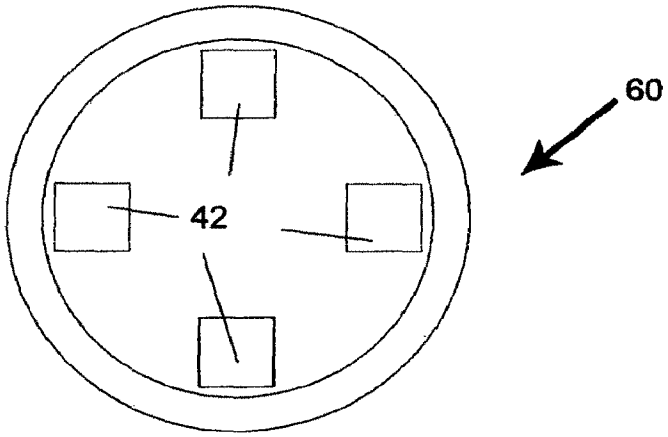
FIGS. 12 and 13 are sectional and top plan views of a third type of test capsule.
Figure 12:
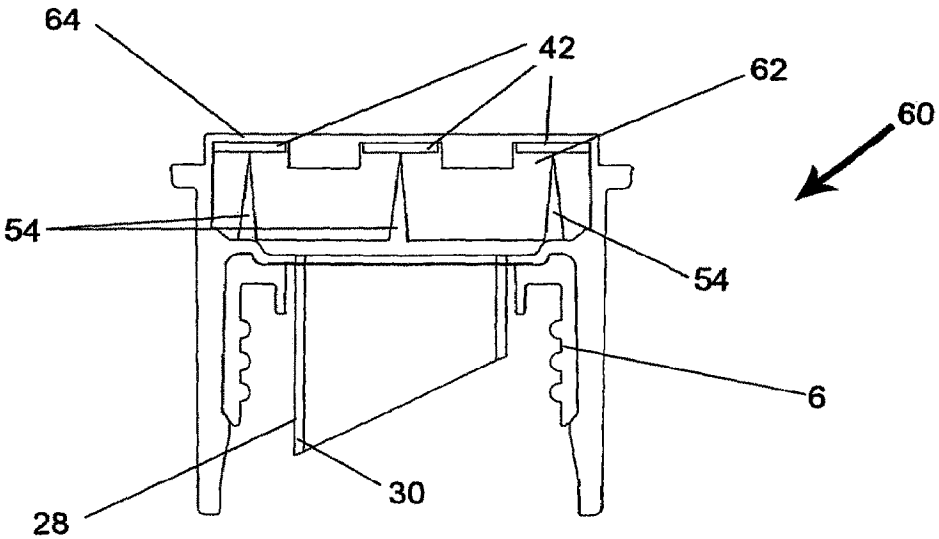

FIGS. 12 and 13 show a test capsule 60 with result portions 42 mounted on conical pins 54 extending into a trough 62 in a top part 64 of the test capsule 60.

The apparatus 2 may be such that the test capsule 10 includes all appropriate parts as disclosed in WO 2011/157981 A1.

It is to be appreciated that the embodiments of the invention described above with reference to the accompanying drawings have been given by way of example only and that modifications may be effected. Thus, for example, the container 4 may be shorter and of a larger diameter than the container 4 shown. The first securing means 8 and the second securing means 12 may be different from those shown. Other types of response chart 14 and result chart 16 may be employed. Instead of using the result chart 16, results may be obtained electronically for example using digital read-out result means. Individual components shown in the drawings are not limited to use in their drawings and they may be used in other drawings and in all aspects of the invention.

The invention claimed is:

1. [Apparatus] *An apparatus* for testing a liquid specimen, which apparatus comprises:

(i) a container for the liquid specimen;

(ii) a lid for closing the container after the liquid specimen has been provided in the container;

(iii) first securing means by which the lid is secured to the container;

(iv) a test capsule for securing to the lid when the lid is on the container;

(v) second securing means by which the test capsule is secured to the lid; and (vi) a response chart which is operable in response to contact with the liquid specimen[,]*;* the apparatus being such that:

(vii) the lid has an openable portion which when opened permits a liquid specimen in the container to enter the test capsule;

(viii) the response chart is inside the test capsule and is contacted by the liquid specimen when the liquid specimen enters the capsule;

(ix) the test capsule has opener means for opening the openable portion on the lid; and the apparatus being [characterised] *characterized* in that:

(x) the opener means is not able to move with respect to the test capsule, whereby the opener means opens the [operable] *openable* portion when the test capsule is being secured to the lid, and whereby the opener means remains unmoved with respect to the test capsule both before and [otter] *after* the [operable] *openable* portion has been opened by the opener means; [and]

(xi) the opener means is a *hollow* cylinder having a longitudinal axis which extends along[,] a longitudinal axis of the apparatus; and (xii) [the opener means] wherein the cylinder has a diameter such that, when the test capsule is secured to the lid, walls defining the cylinder are [adjacent] *generally parallel to one or more* walls defining the container, [whereby] *and* the opener means [opens] *is configured to open* the openable portion over [substantially the entire] *a* diameter of the container [and thereby allows maximum] *that is sufficient to allow free* flow of the liquid specimen from the container into the test capsule*, and from the test capsule back into the container directly through the interior of the cylinder*.

2. Apparatus according to claim 1 in which the first securing means is a screw operated first securing means.

3. Apparatus according to claim 1 in which the second securing means is a push fit securing means.

4. Apparatus according to claim 1 in which the second securing means causes the test capsule to be permanently secured to the lid in order to minimise the possibility of spillage of the liquid specimen.

5. Apparatus according to claim 3 in which the second securing means comprises an outwardly extending formation on the container, and an inwardly extending formation on the test capsule, in which the outwardly extending formation on the container is a lip which is angled outwardly away from a top of the container, and in which the inwardly extending formation on the test capsule is an inclined bead formation.

6. Apparatus according to claim 1 in which the openable portion of the lid is a foil or a membrane.

7. Apparatus according to claim 1 in which [the opener means of the test capsule is a puncturing formation for puncturing the openable portion of the lid, in which] the puncturing formation is a cylindrical formation having a free end which extends at an angle to the opening portion of the lid, and a [fiat] *flat* section which is opposite the free end and which prevents the formation of a complete cut circle and thereby causes a hinge to be created in the openable portion of the lid.

8. Apparatus according to claim 1 and including a result chart for use with the response chart.

9. Apparatus according to claim 8 in which the result chart is outside of the test capsule.

10. Apparatus according to claim 9 in which the result chart fits on the test capsule, in which the result chart has a central aperture, in which the test capsule, has a reduced portion and a shoulder, and in which the result chart fits over the reduced portion and abuts against the shoulder.

11. Apparatus according to claim [6] *8* in which the result chart comprises result sectors, each result sector is for indicating the result of a different test for the liquid specimen, and each result sector has a plurality of differently [coloured] *colored* result portions, and the different [colours] *colors* of the result portions in each result sector indicate different degrees of result for the test afforded by the result sector.

12. Apparatus according to claim 1 in which the container is a tube of a diameter for fitting into laboratory test equipment.

13. Apparatus according to claim 1 in which the response chart comprises response portions which are contacted by the liquid specimen, which become differently coloured to indicate different characteristics present in the liquid specimen, and which are read at predetermined time intervals.

14. Apparatus according to claim 1 in which the response chart is inside the test capsule such that the response chart is in a test chamber.

15. Apparatus according to claim [1] *8* in which the result chart comprises result sectors, each result sector is for indicating the result of a different test for the liquid specimen, and each result sector has a plurality of differently [coloured] *colored* result portions, and the different [colours] *colors* of the result portions in each result sector indicate different degrees of result for the test afforded by the result sector, the response chart comprises response portions which are contacted by the liquid specimen, which become differently [coloured] *colored* to indicate different characteristics present in the liquid specimen, and which are read at predetermined time intervals, and including aligning means for aligning one of the result sectors with one of the response portions such that each one of the result sectors has its own one of the response portions.

*16. The apparatus according to claim 1, in which the opener means opens the openable portion over substantially the entire diameter of the container and thereby allows maximum flow of the liquid specimen from the container into the test capsule.*

*17. The apparatus according to claim 1, in which the opener means has a generally cylindrical shape.*

*18. The apparatus according to claim 1, in which the test capsule has a generally cylindrical shape.*

*19. The apparatus according to claim 1, in which the container has a generally cylindrical shape.*

*20. An apparatus for testing a liquid specimen, which apparatus comprises:*

*(i) a container for the liquid specimen;*

*(ii) a lid for closing the container after the liquid specimen has been provided in the container;*

*(iii) first securing means by which the lid is secured to the container;*

*(iv) a test capsule for securing to the lid when the lid is on the container;*

*(v) second securing means by which the test capsule is secured to the lid; and*

*(vi) a response chart which is operable in response to contact with the liquid specimen;*

*the apparatus being such that:*

*(vii) the lid has an openable portion which when opened permits a liquid specimen in the container to enter the test capsule;*

*(viii) the response chart is inside the test capsule and is contacted by the liquid specimen when the liquid specimen enters the capsule;*

*(ix) the test capsule has opener means for opening the openable portion on the lid;*

*and the apparatus being characterized in that:*

*(x) the opener means is not able to move with respect to the test capsule, whereby the opener means opens the openable portion when the test capsule is being secured to the lid, and whereby the opener means remains unmoved with respect to the test capsule both before and after the openable portion has been opened by the opener means; and*

*(xi) the opener means is a hollow cylinder having an interior, cylinder walls, and a longitudinal axis which extends along a longitudinal axis of the apparatus; and*

*(xii) wherein the cylinder walls defining the cylinder are generally parallel to walls defining the container, and the opener means is configured to open the openable portion sufficiently to allow flow of the liquid specimen from the container into the test capsule and from the test capsule back into the container, directly through the interior of the cylinder; and*

*(xiii) a response chart inside the test capsule, the response chart comprising a plurality of result portions, the result portions mounted on raised platforms, wherein the platforms carrying the response portions are mutually spaced in the test capsule.*

*21. The apparatus according to claim 20 in which the first securing means is a screw operated first securing means.*

*22. The apparatus according to claim 20 in which the second securing means is a push fit securing means.*

*23. The apparatus according to claim 22 in which the second securing means comprises an outwardly extending formation on the container, and an inwardly extending formation on the test capsule, in which the outwardly extending formation on the container is a lip which is angled outwardly away from a top of the container, and in which the inwardly extending formation on the test capsule is an inclined bead formation.*

*24. The apparatus according to claim 20 in which the second securing means causes the test capsule to be permanently secured to the lid in order to minimize the possibility of spillage of the liquid specimen.*

*25. The apparatus according to claim 20 in which the openable portion of the lid is a foil or a membrane.*

*26. The apparatus according to claim 20 in which the opener means of the test capsule is a puncturing formation for puncturing the openable portion of the lid, in which the puncturing formation is a cylindrical formation having a free end which extends at an angle to the opening portion of the lid, and a flat section which is opposite the free end and which prevents the formation of a complete cut circle and thereby causes a hinge to be created in the openable portion of the lid.*

*27. The apparatus according to claim 20 and including a result chart for use with the response chart.*

*28. Apparatus according to claim 27 in which the result chart is outside of the test capsule.*

*29. Apparatus according to claim 28 in which the result chart fits on the test capsule, in which the result chart has a central aperture, in which the test capsule, has a reduced portion and a shoulder, and in which the result chart fits over the reduced portion and abuts against the shoulder.*

*30. Apparatus according to claim 27 in which the result chart comprises result sectors, each result sector is for indicating the result of a different test for the liquid specimen, and each result sector has a plurality of differently colored result portions, and the different colors of the result*

*portions in each result sector indicate different degrees of result for the test afforded by the result sector.*

*31. The apparatus according to claim 27 in which the result chart comprises result sectors, each result sector is for indicating the result of a different test for the liquid specimen, and each result sector has a plurality of differently colored result portions, and the different colors of the result portions in each result sector indicated different degrees of result for the test afforded by the result sector, the response chart comprises response portions which are contacted by the liquid specimen, which becomes differently colored to indicate different characteristics present in the liquid specimen, and which are read at predetermined time intervals, and including aligning means for aligning one of the result sectors with one of the response portions such that each one of the result sectors has its own one of the response portions.*

*32. The apparatus according to claim 20 in which the container is a tube of a diameter for fitting into laboratory test equipment.*

*33. The apparatus according to claim 20 in which the response chart comprises response portions which are contacted by the liquid specimen, which become differently colored to indicate different characteristics present in the liquid specimen, and which are read at predetermined time intervals.*

*34. The apparatus according to claim 20 in which the response chart is inside the test capsule such that the response chart is in a test chamber.*

* * * * *